(12) United States Patent
Toopcham

(10) Patent No.: US 11,753,442 B2
(45) Date of Patent: Sep. 12, 2023

(54) ANGIOTENSIN I-CONVERTING ENZYME (ACE) INHIBITORY PEPTIDES

(71) Applicant: Thai Union Group Public Company Limited, Samutsakorn (TH)

(72) Inventor: Tidarat Toopcham, Bangkok (TH)

(73) Assignee: Thai Union Group Public Company Limited, Samutsakorn (TH)

( * ) Notice: Subject to any disclaimer, the term of this patent is extended or adjusted under 35 U.S.C. 154(b) by 0 days.

(21) Appl. No.: 17/109,056

(22) Filed: Dec. 1, 2020

(65) Prior Publication Data

US 2022/0169679 A1 Jun. 2, 2022

(51) Int. Cl.
| | |
|---|---|
| C07K 7/06 | (2006.01) |
| C07K 1/12 | (2006.01) |
| C07K 1/16 | (2006.01) |
| A23J 1/12 | (2006.01) |
| A23L 33/18 | (2016.01) |
| A23J 1/04 | (2006.01) |
| A61K 38/00 | (2006.01) |

(52) U.S. Cl.
CPC .................. *C07K 7/06* (2013.01); *A23J 1/04* (2013.01); *A23J 1/125* (2013.01); *A23L 33/18* (2016.08); *C07K 1/12* (2013.01); *C07K 1/16* (2013.01); *A61K 38/00* (2013.01); *C12Y 304/21* (2013.01)

(58) Field of Classification Search
None
See application file for complete search history.

(56) References Cited

U.S. PATENT DOCUMENTS

2003/0148923 A1   8/2003   Osajima et al.

FOREIGN PATENT DOCUMENTS

| CN | 102051399 A | 5/2011 |
| CN | 110732018 A | 1/2020 |
| CN | 110759965 A | 2/2020 |
| JP | 03-787585 B2 | 6/2006 |
| KR | 1404872 B1 | 6/2014 |
| KR | 2015036167 A | 4/2015 |

OTHER PUBLICATIONS

Lee et al.,"A novel angiotensin 1 converting enzyme inhibitory peptide from tuna frame protein hydrolysate and its antihypertensive effect in spontaneously hypertensive rats," Hood Chemistry 118:96-102,2010.*
Balti et al., "Three novel angiotensin I-converting enzyme (ACE) inhibitory peptides from cuttlefish (*Sepia officinalis*) using digestive proteases," *Food Research International* 43: 1136-1143, 2010.
Byun et al., "Structure and Activity of Angiotensin I Converting Enzyme Inhibitory Peptides Derived from Alaskan Pollack Skin," *Journal of Biochemistry and Molecular Biology* 35(2): 239-243, 2002.
Charoenphun et al., "Determination of reaction kinetics of hydrolysis of tilapia (*Oreochromis niloticus*) protein for manipulating production of bioactive peptides with antioxidant activity, angiotensin-I-converting enzyme inhibitory activity and Ca-binding properties," *International Journal of Food Science and Technology* 48: 419-428, 2013.
Chen et al., "Purification and characterization of a novel angiotensin-I converting enzyme (ACE) inhibitory peptide derived from enzymatic hydrolysate of grass carp protein," *Peptides* 33: 52-58, 2012.
Darewicz et al., "Angiotensin I-Converting Enzyme (ACE) Inhibitory Activity and ACE Inhibitory Peptides of Salmon (*Salmo salar*) Protein Hydrolysates Obtained by Human and Porcine Gastrointestinal Enzymes," *Int. J. Mol. Sci.* 15: 14077-14101, 2014.
Fujita et al., "LKPNM: a prodrug-type ACE-inhibitory peptide derived from fish protein," *Immunopharmacology* 44: 123-127, 1999.
Fujita et al., "Classification and Antihypertensive Activity of Angiotensin I-Converting Enzyme Inhibitory Peptides Derived from Food Proteins," *Journal of Food Science* 65(4): 564-569, 2000.
Ghassem et al., "Purification and identification of ACE inhibitory peptides from Haruan (*Channa striatus*) myofibrillar protein hydrolysate using HPLC-ESI-TOF MS/MS," *Food Chemistry* 129: 1770-1777, 2011.
Guang et al., "Plant Food-Derived Angiotensin I Converting Enzyme Inhibitory Peptides," *J. Agric. Food Chem.* 57: 5113-5120, 2009.
Iwaniak et al., "Animal and Plant Proteins as Precursors of Peptides with ACE Inhibitory Activity—An *in silico* Strategy of Protein Evaluation," *Food Technol. Biotechnol.* 47(4): 441-449, 2009.
Liu et al., "Studies on bioactive peptide from Chinese soft-shelled turtle (*Pelodiscus sinensis*) with functionalities of ACE inhibition and antioxidation," *African Journal of Biotechnology* 11(25):6723-6729, 2012.
Murray et al., "Angiotensin Converting Enzyme Inhibitory Peptides Derived from Food Proteins: Biochemistry, Bioactivity and Production," *Current Pharmaceutical Design* 13: 773-791, 2007.
Nakajima et al., "Comparison of ACE inhibitory and DPPH radical scavenging activities of fish muscle hydrolysates," *Food Chemistry* 114: 844,851, 2009.
Natesh et al., "Crystal structure of the human angiotensin-converting enzyme-lisinopril complex," *Nature* 421: 551-554, 2003.
Ondetti et al., "Enzymes of the Renin-Angiotensin System and Their Inhibitors," *Ann. Rev. Biochem.* 51: 283-308, 1982.
Sun et al., "Preparation and Identification of ACE Inhibitory Peptides from the Marine Macroalga *Ulva intestinalis*," *Mar. Drugs* 17: 179, 2019 (17 pages).

(Continued)

*Primary Examiner* — Maury A Audet
(74) *Attorney, Agent, or Firm* — SEED INTELLECTUAL PROPERTY LAW GROUP LLP

(57) ABSTRACT

The present disclosure provides fish-derived peptides with ACE inhibitory activity, and methods of producing peptide isolates comprising the fish-derived peptides. The present disclosure also provides pharmaceutical products, dietary supplements, and functional foods including the peptide isolates, and method of lowering blood pressure of a subject by administering to the subject one or more of the fish-derived peptides.

14 Claims, 3 Drawing Sheets
Specification includes a Sequence Listing.

(56) References Cited

OTHER PUBLICATIONS

Toopcham et al., "Characterizataion and identification of angiotensin I-converting enzyme (ACE) inhibitory peptides derived from tilapia using *Virgibacillus halodenitrificans* SKI-3-7 proteinases," *Journal of Functional Foods* 14: 435-444, 2015.
Wang et al., "Novel ACE Inhibitory Peptides Derived from Simulated Gastrointestinal Digestion in Vitro of Sesame (*Sesamum indicum L.*) Protein and Molecular Docking Study," *Int. J. Mol. Sci.* 21: 1059, 2020 (19 pages).
Wijesekara et al., "Purification and identification of antihypertensive peptides from seaweed pipefish (*Syngnathus schlegeli*) muscle protein hydrolysate," *Food Research International* 44: 703-707, 2011.
Wu et al., "Purification and identification of novel angiotensin-I-converting enzyme inhibitory peptides from shark meat hydrolysate," *Process Biochemistry* 43: 457-461, 2008.
Lee et al., "A novel angiotensin I converting enzyme inhibitory peptide from tuna frame protein hydrolysate and its antihypertensive effect in spontaneously hypertensive rats," *Food Chemistry* 118:96-102, 2010.
Saadi et al., "Recent advances in food biopeptides: Production, biological functionalities and therapeutic applications," *Biotechnology Advances* 33:80-116, 2015.
Tacias-Pascacio et al., "Use of Alcalase in the production of bioactive peptides: A review," *International Journal of Biological Macromolecules* 165:2143-2196, 2020.

\* cited by examiner

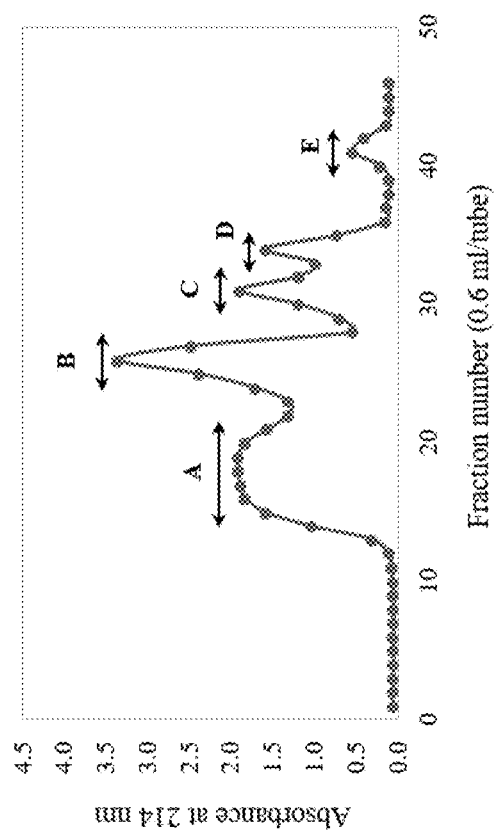
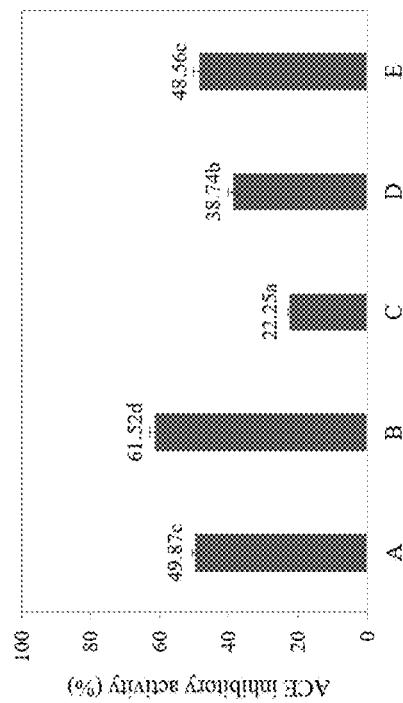
Figure 1
Figure 2

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: ACE inhibitor

<400> SEQUENCE: 1

Val Tyr Ala Pro
1

<210> SEQ ID NO 2
<211> LENGTH: 4
<212> TYPE: PRT
<213> ORGANISM: Artificial Sequence
<220> FEATURE:
<223> OTHER INFORMATION: ACE inhibitor

<400> SEQUENCE: 2

Val Ile Ile Phe
1

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide NR6

<400> SEQUENCE: 3

Asn Leu Leu Pro His Arg
```

```
<210> SEQ ID NO 4
<211> LENGTH: 8
<212> TYPE: PRT
<213> ORGANISM: Artificial Sequence
<220> FEATURE:
<223> OTHER INFORMATION: Synthetic peptide VR8

<400> SEQUENCE: 4

Val Ser Val Val Gln Tyr Ser Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide VR9

<400> SEQUENCE: 5

Val Ile Tyr Ser Arg Ile Asn Cys Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Ile Tyr Ser Arg
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Ile Asn Cys Arg
1

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ser Arg Ile Asn Cys Arg
1               5

<210> SEQ ID NO 9
<211> LENGTH: 8
<212> TYPE: PRT
<213> ORGANISM: Artificial Sequence
<220> FEATURE:
<223> OTHER INFORMATION: ACE inhibitor peptide

<400> SEQUENCE: 9

Phe Phe Gly Arg Cys Val Ser Pro
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: ACE inhibitor peptide

<400> SEQUENCE: 10

Phe Lys Gly Arg Tyr Tyr Pro
1               5

<210> SEQ ID NO 11
<211> LENGTH: 8
<212> TYPE: PRT
<213> ORGANISM: Artificial Sequence
<220> FEATURE:
<223> OTHER INFORMATION: ACE inhibitor peptide

<400> SEQUENCE: 11

Asn Gly Thr Trp Phe Glu Pro Pro
1               5

<210> SEQ ID NO 12
<211> LENGTH: 5
<212> TYPE: PRT
<213> ORGANISM: Artificial Sequence
<220> FEATURE:
<223> OTHER INFORMATION: ACE inhibitor peptide

<400> SEQUENCE: 12

Leu Lys Pro Asn Met
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Gly Pro Leu Tyr His Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Leu Ile His Ala Ile Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ser Phe Leu Met Arg Lys
1               5
```

```
<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Val Leu Met Ser Gln Val Phe Lys Gln Thr
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Trp Thr Ile His Thr Pro
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Leu Pro Pro Gly Lys Ile Val
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Ile Phe Glu Arg Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Phe Asp Gln Phe Leu Pro Ile His
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Asn Gly Pro Ser Gly Gln Thr Gly
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Leu Leu Asp His Arg Ala Asn Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Ala Pro Pro His Ile Phe
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

His Phe Ala Ala Ser Gly Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Leu Glu Gln Val Ser Ala Gly Thr Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Val Gln Ser Val Pro Ala Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Val Glu Trp Lys Glu Arg Ala Thr Glu
1               5

<210> SEQ ID NO 28
```

<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Leu Leu His Ala Lys Pro Leu Asn
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide

<400> SEQUENCE: 29

Ile Lys Val Gly Gly Glu Arg Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Lys Lys Leu Glu Lys Lys Thr Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Gly Val Pro Gly Ile His Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide

<400> SEQUENCE: 32

Gln Gly Pro Pro Gly Asn Pro Gly
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Met Thr Gly Leu Pro Gly Pro Thr Gly Pro
1               5                   10

<210> SEQ ID NO 34
<211> LENGTH: 6

```
<212> TYPE: PRT
<213> ORGANISM: Artificial Sequence
<220> FEATURE:
<223> OTHER INFORMATION: Synthetic peptide

<400> SEQUENCE: 34

Val Ser Val Val Gln Val
1               5
```

US 11,753,442 B2

ANGIOTENSIN I-CONVERTING ENZYME (ACE) INHIBITORY PEPTIDES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 900256_406_SEQUENCE_LISTING.txt. The text file is 5.4 KB, was created on Jan. 18, 2021, and is being submitted electronically via EFS-Web.

BACKGROUND

Technical Field

The present invention relates to a method for preparing fish-derived peptides with ACE inhibitory activity, which may be used as active ingredients in pharmaceutical preparations, dietary supplements, or as food ingredients.

Description of the Related Art

Hypertension or high blood pressure is defined as a systolic blood pressure ≥140 mm Hg and a diastolic blood pressure ≥90 mm Hg. It has been considered as the most common serious chronic health and is one of the major risk factors for cardiovascular diseases (CVD), including stroke, coronary artery disease, heart failure, atrial fibrillation, and peripheral vascular disease. The global prevalence of hypertension is expected that up to 1.58 billion adult patients will suffer from hypertension in 2025 (WHO, 2011). Nowadays, hypertension is mainly treated by lifestyle modification and pharmacological treatment with antihypertensive drugs (Hermansen, 2000). While there are many causes of hypertension, it is well recognized that angiotensin I-converting enzyme (ACE), a dipeptidyl carboxypeptidase (EC 3.4.15.1), plays important roles in renin-angiotensin and kallikrein-kinin systems for the regulation of blood pressure as well as fluid and salt balance in mammals (Vercruysse et al., 2005). It elevates blood pressure by cleaving a dipeptide His-Leu from inactive decapeptide angiotensin I into the potent vasoconstrictor angiotensin II via the renin-angiotensin system. Additionally, it also converts the vasodilator bradykinin into an inactive peptide via the kallikrein-kinin systems (Wang et al., 2008). Thus, inhibition of ACE activity is a major target to reduce mortality in patients with hypertension. Although the ACE inhibitory potency of food-derived peptides are not as great as drugs commonly used in the treatment of hypertension, they are naturally derived from food protein sources, and considered to be milder and safer without the side effects as compared with drugs. Therefore, food protein-derived ACE inhibitory peptides show great promise in the development of novel physiologically functional food for preventing hypertension as well as for therapeutic purposes.

Up to now, an increasing number of ACE inhibitory peptides have been detected in protein hydrolysate prepared from animal and plant proteins (Iwaniak and Dziuba, 2009; Murray and FitzGerald, 2007). Among them, it is well established that fish muscle proteins are an excellent source of ACE inhibitory peptides (Charoenphun, Youravong, and Cheirsilp, 2013; Chen, Wang, Zhong, Wu, and Xia, 2012; Wijesekara, Qian, Ryu, Ngo, and Kim, 2011). Moreover, the attempt to identify and characterize ACE inhibitory peptides derived from various protein hydrolysates to access the structure-activity relationship has increased. However, the structure-activity relationship of ACE inhibitory peptides has not been yet established due to a large variety of ACE inhibitory peptides with different amino acid sequences have been identified. So far, the fish peptides showing ACE inhibitory and antihypertensive activities have been obtained. Nakajima et al. (2009) evaluated ACE inhibitory activity of fish protein hydrolysates derived from fish including Atlantic salmon, coho salmon, Alaska pollack, and southern blue whiting using pepsin, pancreatin, and thermolysin. ACE was inhibited by thermolysin-hydrolyzed Atlantic salmon and coho salmon at $IC_{50}$ values of 0.078 and 0.138 mg/mL, respectively. Wu et al. (2008) reported that shark meat hydrolysate obtained with protease SM98011 digestion showed high ACE inhibitory activity ($IC_{50}$ value of 0.4 mg/mL), comparing to the untreated shark slurry ($IC_{50}$ value of 10.5 mg/mL). The sequences of CF, EY, and FE were confirmed to be novel ACE inhibitory peptides, with $IC_{50}$ values of 1.96, 2.68 and 1.45 µM, respectively. All of which were dipeptides and have a hydrophobic amino acid residue, Phe or Tyr, at the C-terminal position. Balti et al. (2010) showed ACE inhibitory activity of the sequences of VYAP (SEQ ID NO: 1), VIIF (SEQ ID NO: 2) and MAW ($IC_{50}$ values of 6.1, 8.7 and 16.32 respectively), isolated from cuttlefish (*Sepia officinalis*) muscle hydrolysate.

Gastrointestinal (GI) digestion is of particular importance in the bioavailability of ACE inhibitory peptides. After oral ingestion, gastrointestinal enzymes may break up peptides, thereby increasing or decreasing their activity. The purpose of the in vitro digestion model is to simulate in a simplistic manner the digestion processes that take place in the mouth, stomach, and small intestine. ACE inhibitory peptides capable of maintaining bioactivity and stability following gastrointestinal processing are needed.

BRIEF DESCRIPTION OF THE DRAWINGS

FIG. 1 is a size exclusion chromatogram of raw dark meat (RDM) hydrolysate eluted with deionized water.

FIG. 2 shows ACE inhibitory activity at the same concentration of 1 mM leucine equivalent of the separated peptide fractions.

DETAILED DESCRIPTION

Figure 3:
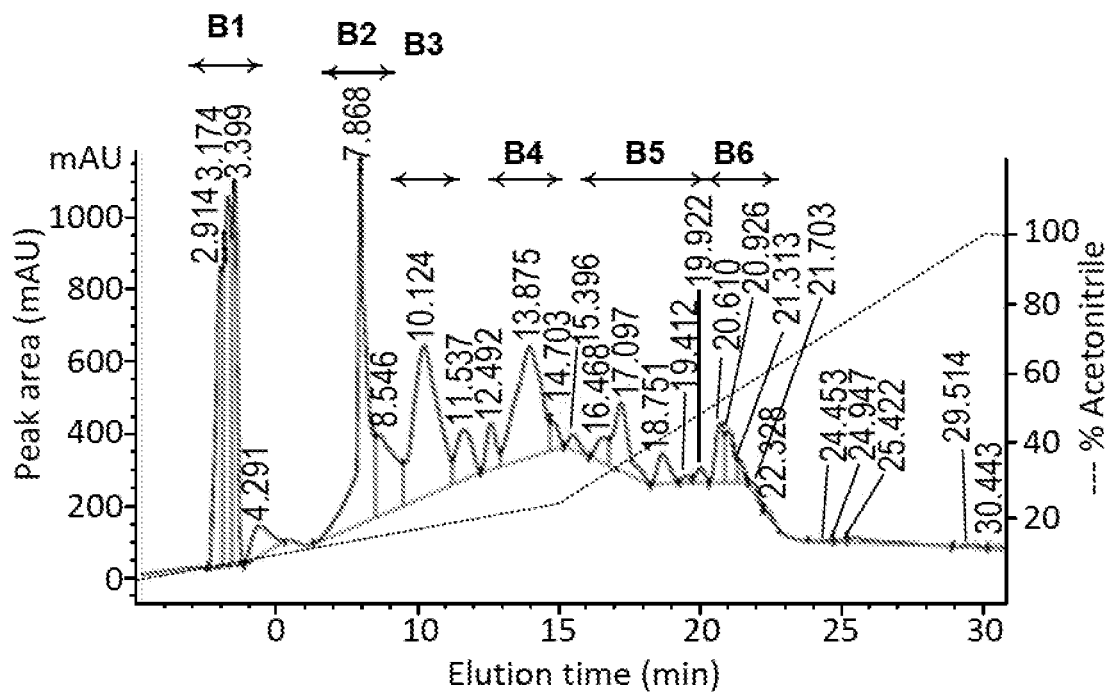
FIG. 3 is a chromatogram of the fraction B eluted with ACN containing 0.1% TFA.

The present disclosure provides fish-derived peptides with ACE inhibitory activity, peptide isolates including the fish-derived peptides, and methods of producing the peptides isolates. Also provided herein are pharmaceutical products, dietary supplements, and functional foods including the fish-derived peptides, and methods of reducing blood pressure using the fish-derived peptides.

As demonstrated in the Examples provided herein, fish-derived peptides of the present disclosure have potent angiotensin I-converting enzyme (ACE) inhibitory activity. In particular, the three peptides exhibiting the most potent ACE inhibitory potency are VIYSRINCR (SEQ ID NO: 5) with an $IC_{50}$ of 0.27 µg/ml (or 0.24 µM), VSVVQYSR (SEQ ID NO: 4) with an $IC_{50}$ of 0.89 µg/ml (or 0.95 µM), and NLLPHR (SEQ ID NO: 3) with an $IC_{50}$ of 0.93 µg/ml (or 1.24 µM). These three novel peptides have stronger potential for ACE inhibition comparing with the reported ACE inhibitory peptides and commercial dietary supplements for ACE inhibition. Additionally, gastrointestinal digestion of the fish-derived peptide VIYSRINCR (SEQ ID NO: 5) produces peptides including VIY, VIYSR (SEQ ID NO: 6), INCR (SEQ ID NO: 7), and SRINCR (SEQ ID NO: 8). The fish-derived peptides with ACE inhibitory activity (including the gastrointestinal digestion products of these peptides) may be used as blood pressure-lowering agent in pharmaceutical products, dietary supplements, and functional foods.

"Fish-derived peptide" refers to a peptide isolated from fish, or a digestion product (e.g., a product of gastrointestinal digestion) of a peptide isolated from fish. Fish are cold-blooded aquatic vertebrates that include the bony fishes and cartilaginous and jawless fishes and that have typically an elongated shaped body terminating in a broad caudal fin, limbs in the form of fins (if present at all), and a 2-chambered heart by which blood is sent through thoracic gills to be oxygenated. In certain embodiments, the fish is a bony fish. Bony fish are of the Superclass Osteichthyes and include freshwater bony fish such as trout, perch, walleye, pike, brim, bass, carp, and certain salmon species. Examples of saltwater bony fish include salmon (e.g., Atlantic salmon, chinook, sockeye, coho, pink, and chum), tuna (e.g., skipjack, bluefin, yellowfin, and albacore), cod (e.g., Atlantic cod and Pacific cod), halibut, and mahi mahi.

In certain embodiments, the fish is tuna. Tuna refers to a saltwater fish that belongs to the tribe Thunnini, a subgrouping of the Scombridae (mackerel) family. The Thunnini tribe comprise 15 species across five genera, which includes the following genera: *Allothunnus*, which are known as slender tunas; the genus *Auxis*, which are also known as frigate tunas; the genus *Euthynnus*, which are also known as little tunas; the genus *Katsuwonus*, which are also known as skipjack tunas; and the genus *Thunnus*, which includes albacores and true tunas. The genus *Thunnus* subgenus *Thunnus* (*Thunnus*), which are also known as bluefin tunas, and the subgenus *Thunnus* (*Neothunnus*), which are also known as yellowfin tunas. In some embodiments, the tuna is of the genus *Katsuwonus* (i.e., is a skipjack tuna).

"Fish meat" refers to muscle tissue of any species of fish. In some embodiments, the meat is raw (i.e., uncooked). In some embodiments, the meat is dark meat. Fish dark meat refers to fish meat rich in myoglobin, which may affect the texture and flavor of the fish meat when cooked. For example, tuna dark meat is thus generally considered as a low-value tuna byproduct in tuna processing due to its undesired flavor and texture. However, as a source for protein or peptide extraction, tuna dark meat is advantageously positioned due to its abundance and low-cost.

"ACE inhibitory activity" refers to the ability to inhibit the activity of angiotensin I-converting enzyme (ACE). In some embodiments, the fish-derived peptides or peptide isolates described herein have an $IC_{50}$ value of ACE inhibition of 100 µg/ml or lower. Method for measuring inhibitory activity against ACE include those described in Example 5.

In some aspects, the present disclosure provides methods of producing a peptide isolate. The methods may include mixing fish meat with water to produce an aqueous mixture; adjusting the pH of the aqueous mixture to a basic pH (i.e., a pH of greater than 7); and hydrolyzing the fish meat by adding an alkaline protease to the aqueous mixture and incubating the aqueous mixture under conditions sufficient to produce a hydrolysate.

"Peptide isolate" refers to a peptide extract or purified peptides derived from cells or tissue, or a peptide extract or purified peptide product that has undergone enzymatic hydrolysis as defined herein.

In some embodiments, the aqueous mixture comprises a ratio of meat to water of about 1:1 to about 1:5. In some embodiments the aqueous mixture comprises a ratio of meat to water of about 1:2 to about 1:5, 1:2 to about 1:4, or about 1:2 to about 1:3.

In some embodiments, the aqueous mixture comprises a protein concentration in a range of about 1% w/v to about 20% w/v (g protein/ml water). In some embodiments, the aqueous mixture comprises a protein concentration in a range of about 1% w/v to about 15% w/v, about 1% w/v to about 10% w/v, about 5% (w/v) to about 20% (w/v), or about 5% (w/v) to about 15% (w/v). In some embodiments, the aqueous mixture comprises a protein concentration of about 10% w/v. Protein concentration may be measured by techniques known in the art, such as by measuring the absorbance at 280 nm spectrophotometry.

As previously noted, the method may include adjusting the pH to a basic pH (i.e., a pH of greater than 7). In some embodiments, the basic pH is in the range of about 7 to about 11. In some embodiments, the basic pH is in the range of about 7 to about 9, or about 8 to about 8.5.

As previously noted, the method may include hydrolyzing the fish meat by adding an alkaline protease to the aqueous mixture and incubating the aqueous mixture under conductions sufficient to produce a hydrolysate.

"Hydrolysate" refers to a product of enzymatic hydrolysis. Enzymatic hydrolysis is the breakdown of compounds (e.g., in a cell or tissue sample) in the presence of enzymes, in the presence of water. A hydrolysate may refer to a product of enzymatic hydrolysis based on the addition of exogenously provided enzymes or may refer to a product of enzymatic hydrolysis based on enzymatic activity of endogenous enzymes. Enzymatic hydrolysis based on enzymatic activity of endogenous enzymes can be referred to as autolysis.

"Protease" is an enzyme that catalyzes proteolysis, which is the breakage of peptide bonds resulting in breakdown of proteins into smaller polypeptides or single amino acids. Proteases can be classified into seven groups: serine proteases, which use a serine alcohol as the reaction nucleophile; cysteine proteases, which use a cysteine thiol as the nucleophile; threonine proteases, which use a threonine secondary alcohol as the nucleophile; aspartic proteases, which use an aspartate carboxylic acid; glutamic proteases, which use a glutamate carboxylic acid; metalloproteases, which use a metal, often zinc; and asparagine peptide lyases, which use an asparagine to perform an elimination reaction (not requiring water).

"Alkaline protease" refers to a protease having enzymatic activity at an alkaline pH (i.e., a pH of greater than 7). Alkaline proteases often have activity at a basic pH of up to about 11. Examples of alkaline proteases include proteinase K, subtilisin, and oryzin.

In some embodiments, the alkaline protease comprises a serine protease. "Serine protease" refers to enzymes that cleave peptide bonds in proteins, in which serine serves as the nucleophilic amino acid at the (enzyme's) active site. Subtilisin is a serine protease that can be obtained from certain soil bacteria such as *Bacillus subtilis* and *Bacillus licheniformis*. Alcalase is a commercially available form of subtilisin derived from *Bacillus licheniformis*.

In some embodiments, the conditions sufficient to produce a hydrolysate comprise incubating the aqueous mixture with the alkaline protease for a time period of at least about an hour. In some embodiments, the time period is in a range of about 2 hours to about 5 hours.

In some embodiments, the conditions sufficient to produce a hydrolysate comprise incubating the aqueous mixture with the alkaline protease comprise incubating at a temperature in the range of about 40° C. to about 70° C.

In some embodiments, the method further includes a step of removing cellular debris from the hydrolysate following the hydrolyzing step.

"Removing cellular debris" refers to the isolation of a soluble product such as a supernatant from a cellular extract. Cellular debris may be removed, for example, by centrifugation and filtration. In some embodiments, removing cellular debris comprises centrifuging and filtering the hydrolysate to obtain a supernatant.

In some embodiments, the hydrolyzing step further includes terminating a hydrolysis reaction by heating the hydrolysate to a temperature in a range of about 80° C. to about 100° C. following the incubating the aqueous mixture under conditions sufficient to produce the hydrolysate. In some embodiments, terminating the hydrolysis reaction includes incubating the hydrolysate at the temperature in the range of about 80° C. to about 100° C. for a time period in a range of about 10 minutes to about 20 minutes. For example, the hydrolysate may be heated to about 90° C. for about 15 minutes. Following termination of the hydrolysis reaction, the hydrolysate may be cooled to a temperature below 40° C., such as to a temperature in a range of about 10° C. to about 30° C.

In some embodiments, the method further comprises a step of subjecting the hydrolysate to chromatography, and collecting one or more chromatography fractions including the peptides with ACE inhibitory activity.

"Chromatography" refers to the separation of a mixture by passing it in solution or suspension or as a vapor (as in gas chromatography) through a medium in which the components move at different rates. Size exclusion chromatography is, a chromatographic method in which molecules in solution are separated by their size, and in some cases molecular weight. Reversed-phase chromatography includes any chromatographic method that uses a hydrophobic stationary phase.

In some embodiments, the method further includes a step of enzymatically digesting the peptide isolate to produce one or more digestion products of the peptides. "Enzymatically digesting" refers to the breakdown of macromolecules into smaller compounds based on the activity of enzymes.

In some embodiments, the enzymatically digesting comprises in silico gastrointestinal digesting. "Gastrointestinal digesting" refers to enzymatic digestion performed by enzymes naturally present in the gastrointestinal tract. Examples of enzymes naturally present in the gastrointestinal tract include pepsin, trypsin and chymotrypsin. In silico gastrointestinal digest refers to an enzymatic digestion by gastrointestinal tract enzymes outside of the gastrointestinal tract, such as in a test tube, using enzymes that have been isolated from a gastrointestinal tract.

In some aspects, the present disclosure provides formulated products comprising a peptide isolate as described herein and a further ingredient such as a pharmaceutically acceptable carrier, diluent, or excipient. Such products may be administered to a subject or consumed by a subject, and include pharmaceutical products (also referred to as "pharmaceutical compositions") and non-pharmaceutical products (also referred to "non-pharmaceutical compositions," e.g., dietary supplements and functional foods). Proper formulation of the product is dependent upon the route of administration chosen.

The formulated products may comprise different types of carriers, excipients, or diluents depending on whether it is to be administered in solid, liquid or aerosol form. The formulations as describe herein (and any additional active agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular embodiments, the product is formulated for oral administration.

A pharmaceutical product refers to a product for use in the treatment for a disease, disorder or condition, or for treating one or more symptoms of the disease, disorder or condition. A non-pharmaceutical product refers to a formulation other than a pharmaceutical product, such as a dietary supplement, or functional food.

"Functional food" (also called a "nutraceutical product") refers to a food with an added function conferred by incorporating new ingredients (e.g., one or more peptide isolates as previously described) that are not typically or traditionally present in the food product.

In some aspects, the present disclosure provides methods of using peptide isolates or formulated products including the peptide isolates as previously described.

"Mammal" includes humans and both domestic animals such as laboratory animals and household pets, (e.g. cats, dogs, swine, cattle, sheep, goats, horses, rabbits), and non-domestic animals such as wildlife and the like. In certain specific embodiments, the mammal is a human. In certain specific embodiments, the mammal is a pet, such as a dog or cat.

A "subject" according to any of the above embodiments is a mammal. Mammals include but are not limited to, domesticated animals (e.g., cows, sheep, cats, dogs, and horses), primates (e.g., human and non-human primates such as monkeys), rabbits, and rodents (e.g., mice and rats). Preferably the subject is a human.

"Treatment," "treating" or "ameliorating" refers to medical management of a condition, disease, or disorder of a subject (e.g., patient) to reduce or eliminate a symptom, reduce the duration, or delay onset or progression of the condition, disease, or disorder.

An "effective amount" refers to an amount of a peptide isolate that provides a desired physiological change, such as a reduction in hypertension. In certain embodiments, the effective amount is a therapeutically effective amount. The desired physiological change may be, for example, a decrease in symptoms of a disease, or a decrease in severity of the symptoms of the disease, or may be a reduction in the progression of symptoms of the disease. In certain embodiments, the desired physiological change does not involve treatment of a disease.

In certain embodiments, the methods include reducing hypertension in a subject comprising administering to the subject a peptide isolate as previously described, a pharmaceutical product as previously described, or a dietary supplement or functional food as previously described.

"Hypertension" refers to high blood pressure. When the heart beats, it creates pressure that forces blood through a network of blood vessels, which include arteries, veins and capillaries. The pressure forcing blood through these vessels is the result of two forces: systolic pressure, which occurs as blood is pumped out of the heart and into the arteries that are part of the circulatory system; and diastolic pressure, which is created as the heart rests between heart beats. Methods of treating hypertension may include reducing elevated blood pressure or hypertension, and reducing the likelihood of developing elevated blood pressure or hypertension. In some embodiments, reducing elevated blood pressure or hypertension includes at least a 1 mmHg reduction, at least a 5 mmHg reduction, or at least a 10 mmHg reduction in the systolic reading; and/or at least a 1 mmHg reduction, at least a 5 mmHg reduction, or at least a 10 mmHg reduction in the diastolic reading. Elevated blood pressure may refer to a blood pressure reading that includes 120 mmHg or greater in the systolic reading, greater than 80 mmHg in the diastolic reading, or both. Hypertension may refer to a blood pressure reading that includes 130 mmHg or greater in the systolic reading, greater than 80 mmHg in the diastolic reading, or both.

In certain embodiments, the methods include promoting healthy blood pressure in a subject comprising administering to the subject a peptide isolate of any of claims 20 to 26, or a pharmaceutical product of claim 27, or a dietary supplement or functional food of claim 28. Healthy blood pressure refers to a blood pressure reading of lower than 120 mmHg for the systolic reading and lower than 80 mmHg for the diastolic reading.

Experimental studies in this invention are as shown below.

EXAMPLES

Example 1

Preparation of Tuna Raw Dark Meat Hydrolysate with ACE Inhibitory Activity

Tuna raw dark meat (RDM) was ground by a cutting machine with a 3 mm cutting head. Ground RDM was prepared at a concentration of 10% w/v (g protein/ml water) and adjusted to pH 8.5 using NaOH. Alcalase 2.4 L was added to the mixture at a concentration of 4% (w/w) of protein substrate. Hydrolysis was carried out at 60° C. for 4 h. The hydrolyzed mixture was heated at 95° C. for 10 min and then centrifuged at 9000 rpm for 20 min. The supernatant was referred to as RDM hydrolysate. The resulting RDM hydrolysate from this hydrolysis condition have total solid content ~8% and protein recovery ~75%. The RDM hydrolysate was evaluated an $IC_{50}$ for ACE inhibitory activity and exhibited an excellent ACE inhibitory potency with an $IC_{50}$ of 61.58 μm/ml. The RDM hydrolysate containing ACE inhibitory peptides was purified by using column chromatography, namely size exclusion chromatography and reversed-phase high performance chromatography.

Example 2

Purification of ACE Inhibitory Peptides

The RDM hydrolysate was firstly purified connected to a fast protein liquid chromatography. Peptides were eluted with deionized water in isocratic mode at a flow rate of 0.4 ml/min. The eluate was collected in 0.6-ml fractions and pooled as shown in FIG. 1. Each pooled fraction was determined the content of α-amino groups (expressed as leucine equivalents) by TNBS method (Adler-Nissen, 1979) and was also analyzed for ACE inhibitory activity at the same concentration of 1 mM leucine equivalent. The RDM hydrolysate was separated into 5 fractions (Fraction A-E, FIG. 1) and fraction B exhibited the highest ACE inhibitory activity ($p<0.05$, FIG. 2), followed by fraction A and E which showed comparable ACE inhibitory activity ($p>0.05$, FIG. 2). Thus, the fraction B was selected for further purification step, namely reversed-phase high-performance liquid chromatography (RP-HPLC). Although many literatures have reported that ACE inhibitory activity was markedly increased with a decrease of molecular weight of peptides (Byun and Kim, 2002; Natesh et al., 2003; Darewicz et al., 2014). However, amino acid sequence and composition of peptides in the hydrolysate could play a more vital role in controlling ACE inhibitory activity.

The second purification, lyophilized powder of the most active fraction B was dissolved in deionized water and was separated by using a SOURCE™ 15RPC ST 4.6/150 column (GE Healthcare, Piscataway, N.J., USA) connected to an Agilent 1260 Infinity HPLC system. The peptide elution was performed by a linear gradient of acetonitrile containing 0.1% trifluoroacetic acid (0-100%) at a flow rate of 0.5 ml/min. 0.5-ml fractions were collected and pooled as shown in FIG. 3. The content of α-amino groups (expressed as leucine equivalents) and ACE inhibitory activity of each pooled fraction were determined. The fraction B was separated based on the basis of hydrophobicity and collected into 6 major fractions (B1-B6, FIG. 3). Based on reversed-phase chromatography (RPC), polar proteins/peptides were eluted first while non-polar proteins/peptides bind to the column. Elution of the bound hydrophobic proteins/peptides was accomplished by increasing the concentration of organic solvent (Gaurav Pratap et al., 2016). Based on the RPC's principle and specific inhibitory activity, fraction B6 with the highest hydrophobicity showed the most potent ACE inhibitory activity (See Table 1). In order to obtain more purity of ACE inhibitory peptides, the fraction B6 was further purified on a Zorbax Eclipse Plus C18 Rapid Resolution column.

TABLE 1

ACE INHIBITORY ACTIVITY OF THE COLLECTED FRACTIONS.

| Fraction | Peptide content* (μg leucine equivalents) | ACE inhibition (%) | Specific inhibitory activity (%/μg leucine eq.) |
|---|---|---|---|
| B1 | 9.84 | 25.04 ± 0.62 | 2.55 ± 0.06[a] |
| B2 | 8.92 | 54.50 ± 1.10 | 6.11 ± 0.12[c] |
| B3 | 8.59 | 47.21 ± 0.94 | 5.49 ± 0.11[b] |
| B4 | 10.17 | 86.07 ± 1.23 | 8.47 ± 0.12[d] |

TABLE 1-continued

ACE INHIBITORY ACTIVITY OF THE COLLECTED FRACTIONS.

| Fraction | Peptide content* (μg leucine equivalents) | ACE inhibition (%) | Specific inhibitory activity (%/μg leucine eq.) |
|---|---|---|---|
| B5 | 5.57 | 70.34 ± 2.08 | 12.62 ± 0.37$^e$ |
| B6 | 1.25 | 66.27 ± 1.00 | 53.18 ± 0.80$^f$ |

Note:
Different letters in the same column indicate significant differences ($p < 0.05$).
*means peptide content in reaction of ACE inhibitory activity assay.

Figure 4:
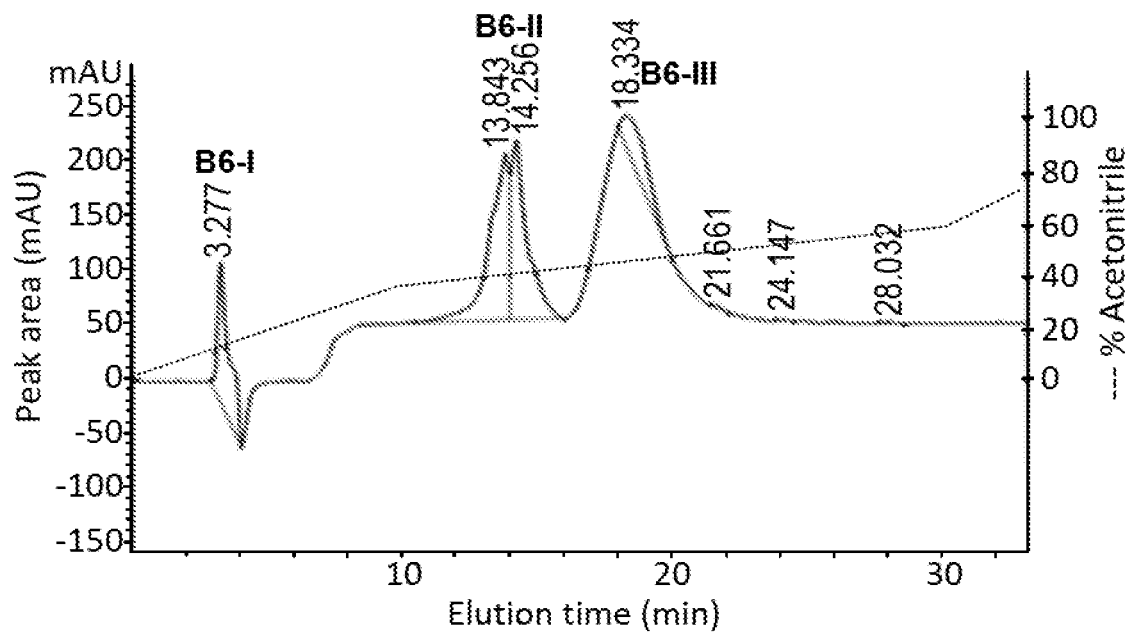
FIG. 4 is a chromatogram of the fraction B6 eluted with ACN containing 0.1% TFA.

The third purification, the fraction B6 showing the highest ACE inhibitory activity (50 μl) was applied to a column (3.5 μm particle size, 4.6×150 mm) connected to a HPLC system. The peptide elution was carried out by a linear gradient of acetonitrile containing 0.1% trifluoroacetic acid (0-100%) at a flow rate of 0.5 ml/min. 0.5-ml fractions were collected and pooled as shown in FIG. 4. The content of α-amino groups (expressed as leucine equivalents) and ACE inhibitory activity of each pooled fraction were determined. The fraction B6 was clearly separated into 3 fractions (Fraction B6-I, B6-II, and B6-III, FIG. 4). When considering at specific inhibitory activity of the peptide fractions against ACE, the fraction B6-II showed the strongest inhibitory activity (see Table 2).

TABLE 2

ACE INHIBITORY ACTIVITY OF THE COLLECTED FRACTIONS.

| Fraction | Peptide content* (μg leucine equivalents) | ACE inhibition (%) | Specific inhibitory activity (%/μg leucine eq.) |
|---|---|---|---|
| B6-I | 0.35 | 3.54 ± 0.52 | 10.28 ± 1.10$^a$ |
| B6-II | 0.38 | 23.41 ± 0.62 | 62.42 ± 0.84$^c$ |
| B6-III | 0.73 | 21.67 ± 0.34 | 29.72 ± 0.24$^b$ |

Note:
Different letters in the same column indicate significant differences ($p < 0.05$).
*means peptide content in reaction of ACE inhibitory activity assay.

In order to obtain peptide sequences containing in the purified peptide fraction exhibiting an excellent ACE inhibitory activity, the purified peptide fractions selected for peptide sequencing by using liquid chromatography tandem mass spectrometry (LC-MS/MS) were the fraction B2 and B4 from the 1$^{st}$ purification due to their high ACE inhibitory activity and high peptide yield, and the fraction B6-II from the 2$^{nd}$ purification due to the highest ACE inhibitory potency.

Example 3

Identification of ACE Inhibitory Peptides

Amino acid sequence of the purified peptide fractions from fraction B2, B4, and B6-II was identified by using liquid chromatography tandem mass spectrometry. In order to verify ACE inhibitory activity of the identified peptides and gain better understanding on the structure-activity relationship, the peptides identified from LC-MS/MS were chosen as shown in Table 3 and chemically synthesized using a solid phase peptide synthesis method. The purity of the synthesized peptides was greater than 98% as determined via HPLC analysis. The molecular mass of the synthesized peptides was confirmed by the manufacturer using liquid chromatography coupled to a mass spectrometer. The ACE inhibitory activity of each synthesized peptide was determined. Amino acid sequence of the synthesized peptides was subjected to in silico ACE inhibitory activity analysis using the BIOPEP database (http://www.uwm.edu.pl/biochemia/index.php/en/biopep).

All synthetic peptides at the same peptide concentration of 1 mg/ml showed ACE inhibitory activity (see Table 3). Different arrangements of amino acid sequence in peptides resulted in different ACE inhibitory potency. These peptides were found to be small peptides with different molecular weights in the range of 600-1000 Da and contained 5-10 amino acids within a peptide fragment.

Previous studies have reported that most ACE inhibitory peptides are small peptides of 2-12 residues and molecular weight less than 3000 Da, which may fit in the ACE active site more easily and thus assert inhibitory activity (Sun et al., 2019). Although di- or tripeptides with high potent ACE inhibitory activity have been widely reported, longer peptides were also found to possess the strong ACE inhibitory activity. For instance, FFGRCVSP (SEQ ID NO: 9) from ovalbumin, FKGRYYP (SEQ ID NO: 10) from chicken muscle, NGTWFEPP (SEQ ID NO: 11) from Human myofibrillar protein, and LKPNM (SEQ ID NO: 12) from dried bonito muscle were discovered (Fujita et al., 2000; Fujita and Yoshikawa, 1999; Ghassem et al., 2011).

Among the synthetic peptides described herein, the first 3 peptides exhibiting the most potent ACE inhibitory activity were VIYSRINCR (SEQ ID NO: 5) with an IC$_{50}$ of 0.27 μg/ml (or 0.24 μM), followed by VSVVQYSR (SEQ ID NO: 4) with an IC$_{50}$ of 0.89 μg/ml (or 0.95 μM) and NLLPHR (SEQ ID NO: 3) with an IC$_{50}$ of 0.93 μg/ml (or 1.24 μM). It should be noted that these 3 synthetic peptides performed stronger inhibition than PeptACE® (IC$_{50}$=144±8 μg/ml, Liu et al., 2012) derived from bonito peptides, a commercial dietary supplement for lowering blood pressure.

In order to evaluate bioavailability of ACE inhibitory peptides, these 3 synthetic peptides were selected for further studies regarding in vitro gastrointestinal (GI) digestion. Moreover, amino acid sequences of peptides as shown in Table 3 were compared with the BIOPEP database where potential ACE inhibitory peptides from various protein sources have been reported. Most of the peptides contained potential ACE inhibitory peptides within their sequences. Moreover, the peptides identified from this invention were found to be novel ACE inhibitory peptides.

Although the structure-activity relationship of ACE inhibitory peptides has not yet been fully established, some common structural features of ACE inhibitory peptides have been reported. The C-terminus of peptides have been suggested to be a controlling factor of the ACE inhibitory activity via interactions with the S$_1$, S'$_1$, and S'$_2$ subsites at the active site of ACE (Ondetti and Cushman, 1982), which typically contain hydrophobic amino acid residues. In addition, the branched aliphatic amino acids at the N-terminal end have been reported to be most effective for increasing the peptide binding activity of ACE (Byun and Kim, 2002). This study found that the peptides possessing Arg (R) at the C-terminal position might play an important role in ACE inhibitory activity which was in agreement with Wang et al. (2020). The positively charged amino acids (Lys and Arg) at the C-terminus has been implied to increase the potency of ACE inhibitory peptides (Guang and Philips, 2009; Toopcham et al., 2015). Additionally, the presence of hydrophobic amino acids with aromatic or branched chain, including Gly (G), Val (V), Trp (W), Leu (L), Phe (F), and Met (M) at the N-terminus, seemed to positively influence ACE inhibitory activity of these synthetic peptides.

TABLE 3

ACE INHIBITORY ACTIVITY OF THE SYNTHETIC PEPTIDES.

| Amino acid sequence | ACE inhibition (%) | ACE inhibitory sequence reported in the literature* |
|---|---|---|
| GPLYHS (SEQ ID NO: 13) | 85.81 ± 1.49[l] | LY, GPL, GP, PL, YH |
| LIHAIL (SEQ ID NO: 14) | 33.43 ± 2.02[d] | Al, IL |
| SFLMRK (SEQ ID NO: 15) | 77.73 ± 1.15[j] | SF |
| VIYSRINCR (SEQ ID NO: 5) | 97.02 ± 0.46[n] | IY, VIY |
| VLMSQVFKQT (SEQ ID NO: 16) | 55.15 ± 1.89[g] | VF, VFK |
| WTIHTP (SEQ ID NO: 17) | 68.03 ± 1.13[h] | TP |
| LPPGKIV (SEQ ID NO: 18) | 71.72 ± 0.12[i] | LPP, GK, PG, PP |
| IFERL (SEQ ID NO: 19) | 45.34 ± 3.61[f] | RL, IF |
| FDQFLPIH (SEQ ID NO: 20) | 88.39 ± 1.30[l] | — |
| NGPSGQTG (SEQ ID NO: 21) | 25.91 ± 2.41[c] | GP, GQ, SG, TG, NG |
| LLDHRANL (SEQ ID NO: 22) | 29.21 ± 1.92[c] | RA |
| APPHIF (SEQ ID NO: 23) | 81.96 ± 2.17[k] | AP, PP, PH, IF |
| HFAASGK (SEQ ID NO: 24) | 27.01 ± 1.44[c] | AA, GK, SG |
| LEQVSAGTT (SEQ ID NO: 25) | 1.90 ± 0.14[a] | AG, GT |
| NLLPHR (SEQ ID NO: 3) | 94.87 ± 0.97[m] | LLP, PH |
| VQSVPAT (SEQ ID NO: 26) | 36.93 ± 1.18[e] | VP |
| VEWKERATE (SEQ ID NO: 27) | 15.52 ± 1.60[b] | RA, VE, TE, EW, KE |
| LLHAKPLN (SEQ ID NO: 28) | 79.01 ± 2.02[jk] | PL, KP, LN |
| VSVVQYSR (SEQ ID NO: 4) | 94.15 ± 0.20[m] | — |
| IKVGGERF (SEQ ID NO: 29) | 24.33 ± 3.38[c] | RF, VG, GE, GG |
| KKLEKKTT (SEQ ID NO: 30) | 21.53 ± 0.66[c] | KL, EK, LEK |
| GVPGIFIGS (SEQ ID NO: 31) | 70.58 ± 2.16[i] | VP, GI, GSGV, HG, PG |
| QGPPGNPG (SEQ ID NO: 32) | 2.91 ± 1.91[a] | GP, QG, PG, GPP, PP, QGP |
| MTGLPGPTGP (SEQ ID NO: 33) | 49.05 ± 1.77[f] | GLP, LPG, GP, GL, TG, PG, PT, TGP |

Note:
Synthetic peptides were tested ACE inhibitory activity at the same concentration of 1 mg/ml.
(—) = not reported. (*) = reported in BIOPEP database.
Different letters in the same column indicate significant differences ($p < 0.05$).

Example 4

Figure 5:
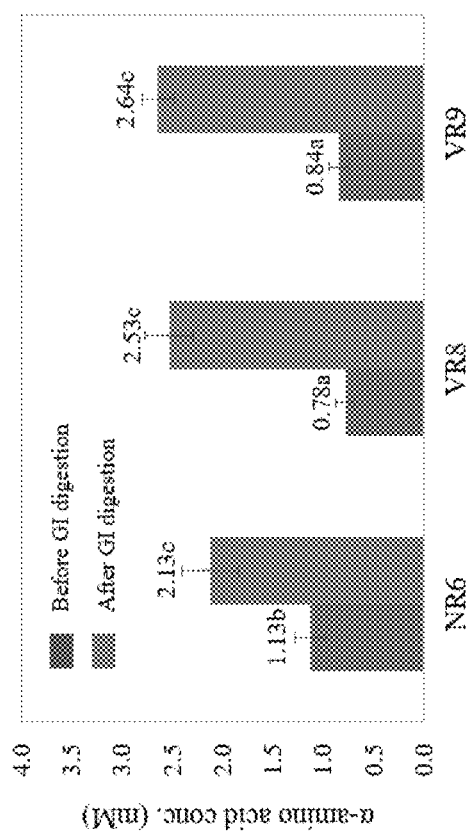
FIG. 5 shows effect of in vitro gastrointestinal (GI) digestion on α-amino group content of synthetic peptides NLLPHR (NR6, SEQ ID NO: 3), VSVVQYSR (VR8, SEQ ID NO: 4), and VIYSRINCR (VR9, SEQ ID NO: 5).
Figure 6:
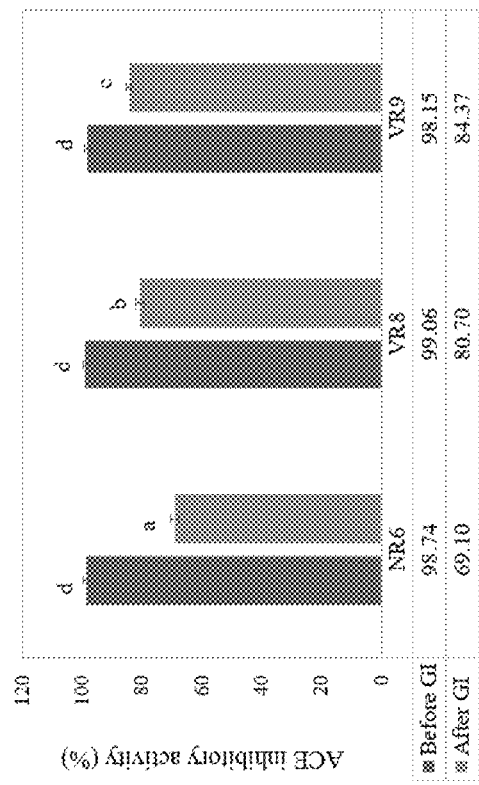
FIG. 6 shows effect of in vitro gastrointestinal (GI) digestion on ACE inhibitory activity of synthetic peptides NLLPHR (NR6, SEQ ID NO: 3), VSVVQYSR (VR8, SEQ ID NO: 4), and VIYSRINCR (VR9, SEQ ID NO: 5).

In Vitro Gastrointestinal (GI) Digestion of the Potent Ace Inhibitory Peptides It is necessary for ACE inhibitory peptides to retain its activity in GI tract so that it can be absorbed into the bloodstream, where the peptide inhibitors can show their hypotensive effect. In vitro gastrointestinal digestion provides an easy process to imitate antihypertensive activity of peptides under oral administration. The 3 synthetic peptides exhibiting the strongest ACE inhibition, namely NLLPHR (NR6, SEQ ID NO: 3), VSVVQYSR (VR8, SEQ ID NO: 4), and VIYSRINCR (VR9, SEQ ID NO: 5), were selected for evaluating the stability of ACE inhibitory peptides towards GI enzymes (pepsin and pancreatin). In vitro GI digestion was simulated according to the method of Zhu et al. (2008) with some modifications. One milligram of each sample was dissolved in 0.5 ml of 0.1 M KCl—HCl, and the pH was adjusted to 2.0 with 6 M HCl. Pepsin (1% enzyme/substrate, w/w) was added, and the mixture was incubated in a shaking water bath at 37° C. for 1 h, and the pH was then adjusted to pH 7.5. Subsequently, pancreatin (2% enzyme/substrate, w/w) was added, and the mixture was further incubated in a shaking water bath at 37° C. for 2 h. The enzyme reaction was terminated by heating at 95° C. for 10 min. The digests were cooled down to room temperature, adjusted volume to the same level and centrifuged at 8000×g for 20 min. ACE inhibitory activity and α-amino groups content of the peptides before and after in vitro GI digestion were measured. After simulated GI digestion, α-amino group content of all synthetic peptides was increased due to the release of small peptides by the action of pepsin and pancreatin enzymes (FIG. 5). Besides, longer peptides could be easily digested by the GI enzymes as a higher α-amino group content was shown (FIG. 5). ACE inhibitory activity of the peptides NR6, VR8, and VR9 after GI digestion were decreased approximately 30%, 19%, and 14%, respectively (FIG. 6). Although these 3 peptides could be digested by GI enzymes and their inhibitory activity were decreased but their high ACE inhibitory potency still remained.

Example 5

In Silico Gastrointestinal (GI) Digestion of the Potent Synthesized Peptides

In order to predict the released amino acid sequence of peptide fragments after GI digestion, in silico GI digestion of the peptides NLLPHR (NR6, SEQ ID NO: 3), VSVVQYSR (VR8, SEQ ID NO: 4), and VIYSRINCR (VR9, SEQ ID NO: 5) was carried out by using a free web application, namely FeptideDB, which is a web application to assist in bioactive peptide discovery of compounds derived from foods. This web-based information center allows user to select suitable enzyme as in silico enzyme digestions (Panyayai et al., 2019). In the present example, the selected GI enzymes used for cleaving the peptide sequences in silico were pepsin, trypsin, and chymotrypsin. Based on the cleavage sites of the GI enzymes, the possible hydrolysis products obtaining from degradation of the peptides NR6, VR8, and VR9 were shown in Table 4. The predicted amino acid sequences were also searched against the bioactive peptide databases regarding ACE inhibitory peptide. Only the peptide VIY has been reported to be an ACE inhibitor. In order to verify the inhibitory activity of the predicted peptides, all predicted peptides releasing from VR9 were selected for determination of ACE inhibitory activity. The results in Table 5 showed that not only the peptide VIY but also other in silico digested peptides exerted ACE inhibitory activity. The peptides VIYSR (SEQ ID NO: 6), INCR (SEQ ID NO: 7), and SRINCR (SEQ ID NO: 8) remarkably exhibited stronger the inhibitory potency than the peptide VIY. This result suggested that the presences of hydrophobic amino acid at the N-terminus and Arg (R) at the C-terminus might enhance the inhibitory potency of the peptides.

TABLE 4

IN SILICO GASTROINTESTINAL DIGESTION OF THE PEPTIDES NLLPHR (NR6, SEQ ID NO: 3), VSVVQYSR (VR8, SEQ ID NO: 4), AND VIYSRINCR (VR9, SEQ ID NO: 5) PREDICTED BY PEPTIDEDB.

| Parent amino acid sequence | Predicted amino acid sequence |
|---|---|
| NLLPHR (SEQ ID NO: 3) | NLL, PHR |
| VSVVQYSR (SEQ ID NO: 4) | VSVVQV (SEQ ID NO: 34), SR |
| VIYSRINCR (SEQ ID NO: 5) | VIY*, VIYSR (SEQ ID NO: 6), INCR (SEQ ID NO: 7), SRINCR (SEQ ID NO: 8) |

Note:
(*) = ACE inhibitory peptide reported in the database.

TABLE 5

ACE INHIBITORY ACTIVITY OF THE SYNTHESIZED PEPTIDES IN WHICH AMINO ACID SEQUENCES OBTAINED FROM IN SILICO GASTROINTESTINAL DIGESTION OF THE PEPTIDE VIYSRINCR (VR9, SEQ ID NO: 5).

| | ACE inhibitory activity (%) | |
|---|---|---|
| Amino acid sequence | At 1 mg/ml | At 1 μg/ml |
| VIY | $18.51 \pm 1.12^a$ | ND |
| VIYSR (SEQ ID NO: 6) | $97.83 \pm 0.79^b$ | $12.05 \pm 2.14^a$ |
| INCR (SEQ ID NO: 7) | $100.79 \pm 0.71^c$ | $29.10 \pm 1.06^c$ |
| SRINCR (SEQ ID NO: 8) | $98.85 \pm 0.97^b$ | $27.50 \pm 0.19^b$ |

Note:
ND = not detected.
Different letters in the same column indicate significant differences ($p < 0.05$).

Determination of Angiotensin I-Converting Enzyme (ACE) Inhibitory Activity

ACE inhibitory activity assay was carried out according to the methods of Cushman and Cheung (1971) and Wu et al. (2002) with some modifications. A reaction mixture containing 50 μl of hydrolysate or peptides, 150 μl of 8.3 mM Hippuryl-L-histidyl-L-leucine (HHL), and 50 μl of ACE (25 mU/ml) was incubated at 37° C. for 1 h. Subsequently, 250 μl of 1 M HCl was added to terminate the reaction. The released hippuric acid (HA) was extracted by adding 2.5 ml ethyl acetate, and the mixture was mixed with a vortex for 1 min and left at room temperature for 1 h. Then, 2 ml of the upper layer was transferred into beaker and dried at 80° C. to remove ethyl acetate. Finally, 1 ml of deionized water was added to dissolve the HA. Absorbance was measured at 228 nm. The percentage of ACE inhibition was calculated as follows:

$$ACE\ \text{inhibition}\,(\%) = \frac{[(A-B)-(C-D)]}{(A-B)} \times 100;$$

where A is the absorbance at 228 nm of a reaction containing ACE without hydrolysate; B is the absorbance at 228 nm of a reaction containing ACE previously inactivated by adding HCl in the absence of hydrolysate; C is the absorbance at 228 nm of a reaction in the presence of ACE and hydrolysate; and D is the absorbance at 228 nm of a reaction containing ACE previously inactivated by adding HCl in the presence of hydrolysate. The $IC_{50}$ was defined as the concentration of inhibitor required to inhibit 50% of the ACE activity. Specific inhibitory activity was calculated as ACE inhibition (%) divided by total peptide content (mg).

Determination of α-Amino Groups Content

Content of α-amino groups was performed according to Adler-Nissen (1979). Purified peptide fraction (50 μl) was mixed with 0.2125 M phosphate buffer pH 8.2 (0.5 ml) and 0.05% TNBS reagent (0.5 ml). The reaction mixture was incubated at 50° C. for 1 h in a water bath. Subsequently, 0.1 M HCl (1 ml) was added to stop the reaction. The mixture was left at room temperature for 30 min before an absorbance at 420 nm was monitored. Leucine was used as a standard. The content of α-amino groups was expressed as leucine equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of producing a peptide isolate, comprising the steps of:
   mixing fish meat with water to produce an aqueous mixture;
   adjusting the pH of the aqueous mixture to a basic pH;
   hydrolyzing the fish meat by adding an alkaline protease to the aqueous mixture and incubating the aqueous mixture under conditions sufficient to produce a hydrolysate, wherein the peptide isolate comprises a peptide consisting of the amino acid sequence of SEQ ID NO:5 (VIYSRINCR).

2. The method of claim 1, wherein the aqueous mixture comprises a ratio of meat to water of about 1:2 to about 1:3.

3. The method of claim 1, wherein the aqueous mixture comprises a protein concentration in a range of about 5% (w/v) to about 15% (w/v) (g protein/ml water).

4. The method of claim 1, wherein the basic pH is in the range of above 7 to about 11.

5. The method of claim 1, wherein the alkaline protease comprises a serine protease.

6. The method of claim 1, wherein the conditions sufficient to produce a hydrolysate comprise incubating for a time period in a range of about 2 hours to about 5 hours.

7. The method of claim 1, wherein the conditions sufficient to produce a hydrolysate comprise incubating at a temperature in the range of about 40° C. to about 70° C.

8. The method of claim 1, wherein the method further includes a step of removing cellular debris from the hydrolysate following the hydrolyzing step.

9. The method of claim 8, wherein the removing cellular debris comprises centrifuging and filtering the hydrolysate to obtain a supernatant.

10. The method of claim 1, wherein the hydrolyzing step further includes terminating a hydrolysis reaction by heating the hydrolysate to a temperature in a range of about 80° C. to about 100° C. following the incubating the aqueous mixture under conditions sufficient to produce the hydrolysate.

11. The method of claim 10, wherein the terminating the hydrolysis reaction includes incubating the hydrolysate at the temperature in the range of about 80° C. to about 100° C. for a time period in a range of about 10 minutes to about 20 minutes.

12. The method of claim 1, wherein the method further comprises a step of subjecting the hydrolysate to chromatography, and collecting one or more chromatography fractions including the peptide consisting of the amino acid sequence of SEQ ID NO:5.

13. The method of claim 1, wherein the fish meat comprises raw fish dark meat, ground fish meat, tuna meat, skipjack tuna meat, or any combination thereof.

14. A method of treating hypertension in a subject in need thereof comprising administering to the subject a peptide, wherein the peptide consists of the amino acid sequence of SEQ ID NO:5.

* * * * *